United States Patent [19]

Soper

[11] 4,056,382
[45] Nov. 1, 1977

[54] METHOD OF CONTROLLING AQUATIC WEEDS

[75] Inventor: Quentin Francis Soper, Indianapolis, Ind.

[73] Assignee: Eli Lilly and Company, Indianapolis, Ind.

[21] Appl. No.: 687,120

[22] Filed: June 9, 1976

Related U.S. Application Data

[63] Continuation-in-part of Ser. No. 531,582, Dec. 11, 1974, abandoned.

[51] Int. Cl.$^2$ .............................................. A01N 9/12
[52] U.S. Cl. .......................................... 71/66; 71/90; 260/306.8 D
[58] Field of Search ................................ 71/66, 67, 90

[56] References Cited

PUBLICATIONS

Kubo et al. J. Agr. Food Chem., vol. 18, 1970, pp. 60–65.

*Primary Examiner*—Lewis Gotts
*Assistant Examiner*—Catherine L. Mills
*Attorney, Agent, or Firm*—Dwight E. Morrison; Everet F. Smith

[57] ABSTRACT

A method of controlling aquatic weeds which comprises adding to a body of water containing the aquatic weeds a substituted thiadiazolylurea in sufficient quantity to kill the weeds.

8 Claims, No Drawings

METHOD OF CONTROLLING AQUATIC WEEDS

CROSS REFERENCE

This application is a continuation-in-part of my copending application Ser. No. 531,582, filed Dec. 11, 1974 now abandoned.

BACKGROUND OF THE INVENTION

1. Field of the Invention

The field of the invention relates to the control of aquatic weeds in canals, rivers, ponds, lakes and impoundments.

2. Description of the Prior Art

The problems of controlling the growth of organisms in aqueous systems are serious and growing daily more severe. Submerged aquatic weeds, for example, cause major problems in irrigation and water distribution systems. The growth of weeds in irrigation canals greatly reduces the conductivity and capacity of such systems, with resulting substantial economic loss. Large sums are therefore currently being spent in the mechanical and other methods of removal of weed growths from irrigation canals, especially in the southern and western parts of the United States.

Because of the great difficulties involved in the mechanical removal of weeds and other undesired forms of aquatic life from irrigation canals, ponds, lakes, impoundments, etc., it has been proposed to utilize chemical control. Accordingly, various types of chemicals have been added to such bodies of water.

In the prior art, British Pat. No. 1,290,223, teaches the use of some thiadiazolylureas substituted in the 5-position of the thiadiazole ring with alkenylthio, alkynylthio, and other substituted thio substituents. The compounds are alleged to be growth regulators and terrestrial herbicides. There is no teaching that the compounds are useful against aquatic weeds and none of the tests described in the document suggest the compounds would be active as aquatic herbicides. In addition, the compounds are structurally different from those included within the scope of the instant application.

Also in the prior art is South African Pat. No. 70/04928 (published July 19, 1971), which teaches thiadiazolyl-(2)-ureas as terrestrial herbicides for the control of monocotyledonous and dicotylendonous weeds and wild grasses. The compounds are alleged to be useful in controlling leguminous weeds, umbelliferous plants, millet, mustard, goosefoot, slender foxtail, and chamomile without damage to crops such as grain. There is no teaching that the compounds would be useful as aquatic herbicides.

In addition, British Pat. No. 1,282,308, is directed to 5-mercapto-1,3,4-thiadiazol-2-ylureas alleged to be herbicidal and useful for pre- or postemergence control of mono- and dicotyledonous weeds. There is no teaching in this patent that the disclosed compounds would be useful as aquatic herbicides.

Further, Offenlegungsschrift No. 2,028,778 (Dec. 23, 1971), discloses thiadiazolylurea herbicides 5-substituted by sulfinyl or sulfonyl groups. These compounds are alleged to be soil and leaf herbicides active against mono- and dicotyledonous weeds pre- and postemergence. The activity is alleged to be selective at rates of 0.5-1 kg./ha. and total at rates of 2-10 kg./ha. There is no teaching that the compounds would be active as aquatic herbicides.

Also in the prior art, Canadian Pat. No. 942751 is directed to 5-alkylsulfinyl or sulfonyl 1,3,4-thiadiazolylureas useful as terrestrial herbicides. The compounds included in this patent are alleged to be total herbicides when applied at rates of 2-10 kg./ha., as well as being active for weeds propagated by seeds when applied at rates of 0.25-1 kg./ha. There is no teaching that the compounds would be useful as aquatic herbicides.

In addition, East German Pat. No. 85,222 (Oct. 12, 1971), teaches 2-ureido-1,3,4-thiadiazoles having herbicidal activity. The compounds are taught as being suitable for general weed control as soil sterilants, as plant growth regulators, for treating the foliage of weeds, for the desiccation of defoliation of crop plants, and as selective terrestrial herbicides (pre- and postemergence), being allegedly particularly useful for selectively combatting weeds in sugar beet and potato cultures, for instance. The compounds are taught as being active against both annual and perennial broadleaved and grassy weeds with the rate of application generally 0.5-5 kg./ha. Again, there is no teaching that the compounds would have utility as aquatic herbicides.

Also in the prior art is Rathgeb et al., U.S. Pat. No. 3,929,816 (Dec. 30, 1975), which discloses 1,3,4-thiadiazolyl-(2)-ureas substituted on the 5-position of the thiadiazole ring with an aliphatic thio or cycloaliphatic thio grouping, the aliphatic or cycloaliphatic moiety being a saturated or unsaturated hydrocarbon radical having at most six carbon atoms, and which may be unsubstituted or substituted by halogen or lower alkoxy. The compounds are alleged to be useful as herbicides for the control of mono- and dicotyl weeds and wild grasses. Only terrestrial plants are alleged to be controlled by the compounds. There is no suggestion the compounds disclosed by this reference would be active as aquatic herbicides.

Another reference in the prior art is Kubo et al., *J. Ag. Food Chem.* 18, 60-65 (1970), which discloses a number of 1,3,4-thiadiazole derivatives alleged to possess herbicidal properties. The compounds of this reference lack the alkyl derivative on the urea nitrogen atom directly attached to the thiadiazole nucleus, and thus the Kubo et al. compounds are outside the generic scope of the compounds of the instant application. Kubo et al. evaluated their compounds by preemergence, postemergence, and irrigated water treatment methods. The irrigated water method was utilized by Kubo et al. in testing the herbicidal activity of their compounds against barnyardgrass, slender spikerush and rice. None of the Kubo et al. 5-(substituted thio) compounds were herbicidal to slender spikerush or rice in the irrigated water method.

Another reference is Belgian Pat. No. 820,724, also identified by Derwent No. 27434W, which reference discloses allegedly new 5-alkylsulfonyl- and 5-alkylsulfinyl-1,3,4-thiadiazolylureas, said to be useful as selective pre- or postemergence herbicides for controlling grasses and broadleaf weeds in groundnuts, potatoes, peas, maize and sorghum. The compounds are thus taught for use as terrestrial herbicides. There is no teaching in the reference that such compounds would be useful as aquatic herbicides.

Yet another reference is German Offenlegungsschrift No. 2407144, also identified by Derwent No. 60587W, which reference discloses herbicidal compositions containing substituted, 1,2,4-triazinones and 3-(5-butylsulfonyl-1,3,4-thiadiazol-2-yl)-1,3-dimethylurea, the compositions taught as being useful for selective postemergence weed control in cereal, potato, tomato and soybean crops. Such use is against terrestrial weels, and there is no teaching which would suggest the use of the 1,3,4-thiadiazol-2-ylurea component of the combination alone as an aquatic herbicide.

The search for an effective aquatic herbicide continues, since there exists a very distinct need for a method of controlling the growth of aquatic weeds.

SUMMARY OF THE INVENTION

The present invention relates to a method of controlling aquatic weeds by adding to the water containing such aquatic weeds an herbicidally-effective amount of a substituted thiadiazolylurea.

DESCRIPTION OF THE PREFERRED EMBODIMENT

This invention relates to a novel method for the control of aquatic weeds. More particularly, this invention relates to a novel method and compositions for the control of aquatic weeds using compounds of the formula

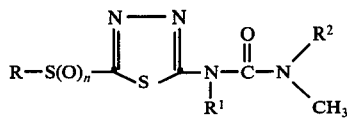 (I)

wherein
R is $C_1$–$C_8$ alkyl, $C_3$–$C_7$ cycloalkyl, or aryl ($C_1$–$C_2$)-alkyl;
$R^1$ is methyl or ethyl;
$R^2$ is hydrogen, methyl or ethyl; and
n is 0, 1 or 2.

The preferred compounds for use in the novel method of this invention are of the formula (I), supra, wherein
R is $C_4$–$C_8$ alkyl;
$R^1$ is methyl;
$R^2$ is hydrogen or methyl; and
n is 0 or 2.

The compounds of choice for use in the novel method of this invention are of the formula (I), supra, wherein
R is $C_6$–$C_8$ alkyl;
$R^1$ is methyl;
$R^2$ is hydrogen or methyl; and
n is 0 or 2.

In the above formula, $C_1$–$C_8$ alkyl is a saturated straight- or branched-chain hydrocarbon radical such as methyl, ethyl, n-propyl, isopropyl, n-butyl, isobutyl, sec.-butyl, t-butyl, n-amyl, sec.-amyl, isoamyl, t-amyl, n-hexyl, isohexyl, sec.-hexyl, n-heptyl, isoheptyl, sec.-heptyl, n-octyl, sec.-octyl, isooctyl and the like.

Also in the above formula, $C_3$–$C_7$ cycloalkyl is a saturated cycloalkyl hydrocarbon radical containing from three to seven carbon atoms and is illustratively cyclopropyl, cyclobutyl, cyclopentyl, cyclohexyl and cycloheptyl.

Aryl ($C_1$–$C_3$)alkyl is illustratively benzyl or phenethyl.

The compounds useful in the novel method and compositions disclosed herein are readily prepared using starting materials and procedures well known to those skilled in the art.

Thus, the compounds useful in the novel aquatic herbicidal process of this invention can be prepared by one or more of the synthesis routes set forth below. The type of product desired will determine the particular synthesis route to be employed.

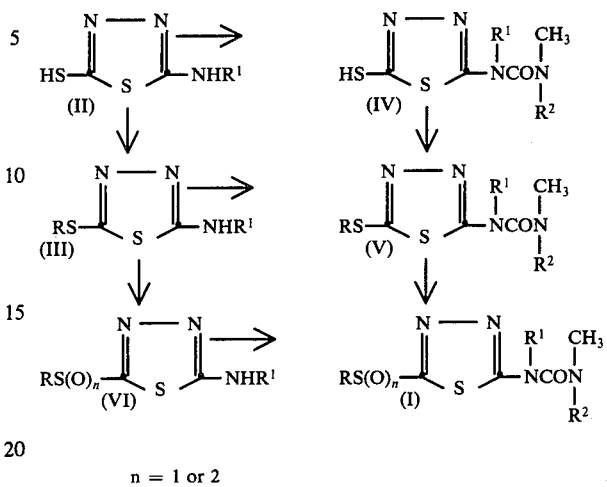

n = 1 or 2

The intermediate compositions corresponding to Structure (II) are synthesized by methods known in the art. For example, such methods are generally taught in publications such as *The Chemistry of Heterocyclic Compounds* V. 4, L. L. Bambas, Interscience Publishers, Inc., New York, 1952, and Petrow et al., *J. Chem. Soc.* 1508 (1958). Methods suitable for preparing the thiadiazol-2-ylurea compounds of Structure (IV) are disclosed in U.S. Pat. No. 3,669,982 (June 13, 1972), which disclosure is hereby incorporated in and made a part of this disclosure. The intermediate compounds having the Structures (III) and (V) may be synthesized from compounds (II) and (IV) by known methods, e.g. reacting compounds (II) and (IV) with alkyl halides and dialkyl sulfates in the presence of a base such as potassium carbonate, sodium hydroxide, potassium hydroxide and the like.

The alkylthio compounds of Structures (V) and (III) may be oxidized to the corresponding sulfones of Structures (I) and (VI), respectively, by oxidizing reagents such as chlorine-acetic acid, chlorine-ferric chloride, potassium permanganate, hydrogen peroxide-acetic acid and the like. By careful control of oxidizing conditions, the sulfoxides of Structures (I) and (VI) are also prepared.

The syntheses of various of the intermediate compounds are exemplified by the following Preparation.

PREPARATION 1

A suspension was prepared of 31 g. of 2-methylamino-5-mercapto-1,3,4-thiadiazole in 316 ml. of 1N alcoholic potassium hydroxide and to the suspension was added 32.9 g. of ethyl iodide. The mixture was refluxed for about 1 hour. The mixture was cooled and filtered and the filtrate concentrated in vacuo. The residue was washed with aqueous sodium carbonate and then extracted with ethyl acetate and the ethyl acetate extracts combined and dried. The drying agent was filtered off and the filtrate concentrated in vacuo to yield 31.5 g. of product having a melting point of about 60°–61° C., and identified by elemental analyses as 2-ethylthio-5-methylamino-1,3,4-thiadiazole.

Following the same general procedure described above, the following additional compounds were prepared.

2-Isopropylthio-5-methylamino-1,3,4-thiadiazole, oil.

2-Methylamino-5-propylthio-1,3,4-thiadiazole, oil.
2-(sec.-Butylthio)-5-methylamino-1,3,4-thiadiazole, oil.
2-Methylamino-5-octylthio-1,3,4-thiadiazole, having a melting point of about 50°–53° C.
2-Cyclohexylthio-5-methylamino-1,3,4-thiadiazole, having a melting point of about 68°–72° C.
2-Benzylthio-5-methylamino-1,3,4-thiadiazole, identified as an oil.
2-Hexylthio-5-methylamino-1,3,4-thiadiazole, having a melting point of about 39°–40° C.
2-Butylthio-5-methylamino-1,3,4-thiadiazole, identified as an oil.
2-Methylamino-5-methylthio-1,3,4-thiadiazole, identified as a semi-solid.

PREPARATION 2

A mixture containing 30 g. of 2-methylamino-5-mercapto-1,3,4-thiadiazole and 11.60 g. of methyl isocyanate in 250 ml. of benzene was refluxed in a 500 ml. flask for a period of about 2 hours. The reaction product mixture was cooled and filtered to obtain 40 g. of a product having a melting point of about 162°–164° C., and identified as 1,3-dimethyl-3-(5-mercapto-1,3,4-thiadiazol-2-yl)urea.

The following Examples are illustrative of the methods of preparation of various compounds for use in the novel aquatic herbicidal method of this invention.

EXAMPLE 1

1,3-Dimethyl-3-(5-butylthio-1,3,4-thiadiazol-2-yl)urea

To a solution of 232.3 g. of 2-butylthio-5-methylamino-1,3,4-thiadiazole in one liter of dry benzene was added 71.5 g. of methyl isocyanate, and the mixture refluxed for about 3 hours. The reaction product mixture was cooled and filtered. The solid obtained on the filter had a melting point of about 83°–84° C., and was identified as 1,3-dimethyl-3-(5-butylthio-1,3,4-thiadiazol-2-yl)urea.

Following the same general procedure of Example 1, and using suitable starting reactants, additional compounds were prepared and identified by elemental analyses.

1A. 1-(5-Ethylthio-1,3,4-thiadiazol-2-yl)-1,3-dimethylurea, having a melting point of about 112°–113° C.

1B. 1,3-Dimethyl-1-(5-propylthio-1,3,4-thiadiazol-2-yl)urea, having a melting point of about 107°–108° C.

1C. 1-(5-Isopropylthio-1,3,4-thiadiazol-2-yl)-1,3-dimethylurea, having a melting point of about 119°–120° C.

1D. 1-(5-sec.-Butylthio-1,3,4-thiadiazol-2-yl)-1,3-dimethylurea, having a melting point of about 118°–119° C.

1E. 1-(5-Hexylthio-1,3,4-thiadiazol-2-yl)-1,3-dimethylurea, having a melting point of about 55°–58° C.

1F. 1,3-Dimethyl-1-(5-octylthio-1,3,4-thiadiazol-2-yl)urea, having a melting point of about 53°–56° C.

1G. 1-(5-Cyclohexylthio-1,3,4-thiadiazol-2-yl)-1,3-dimethylurea, having a melting point of about 112°–114° C.

1H. 1-(5-Benzylthio-1,3,4-thiadiazol-2-yl)-1,3-dimethylurea, having a melting point of about 135°–137° C.

EXAMPLE 2

A solution of 9.3 g. of 1,3-dimethyl-1-(5-sec.-butylthio-1,3,4-thiadiazol-2-yl)urea in 35 ml. of glacial acetic acid was heated to about 85° C., and there was added thereto 10.0 g. of 30 percent hydrogen peroxide dropwise over a period of about 15 minutes. The reaction mixture was stirred at a temperature of about 85°–90° C. for about 1 hour. The reaction mixture was cooled, poured onto ice, and water added to the mixture. The solid material which precipitated was filtered off and air dried. The dried solid was recrystallized from a small amount of ethyl acetate and there was obtained 9.4 g of product having a melting point of about 178°–179° C., and identified by elemental analyses as 1-[5-(sec.-butylsulfonyl)-1,3,4-thiadiazol-2-yl]-1,3-dimethylurea.

Following the same general procedure set forth above and using appropriate starting materials, the following additional compounds were prepared.

2A. 1,3-Dimethyl-1-(5-octylsulfonyl-1,3,4-thiadiazol-2-yl)urea, having a melting point of about 101°–102° C.

2B. 1-(5-Benzylsulfonyl-1,3,4-thiadiazol-2-yl)-1,3-dimethylurea, having a melting point of about 191.5°–192.5° C.

EXAMPLE 3

A mixture containing 5 g. of 1,3-dimethyl-1-(5-mercapto-1,3,4-thiadiazol-2-yl)urea, 3.7 g. of methyl iodide, and 1.7 g. of anhydrous potassium carbonate in 50 ml. of N,N-dimethylformamide, was stirred for about 15 hours at a temperature of about 70° C. The resulting clear reaction product mixture was concentrated under vacuum to a solid, which solid, on recrystallization from ethyl acetate, yielded a product identified as 1,3-dimethyl-1-(5-methylthio-1,3,4-thiadiazol-2-yl)urea, having a melting point of about 154°–156° C.

EXAMPLE 4

To a suspension of 5 g. of 1,3-dimethyl-1-(5-methylthio-1,3,4-thiadiazol-2-yl)urea in 50 ml. of acetic acid was added, dropwise and with stirring, an aqueous solution of potassium permanganate (7.3 g. in 100 ml. of water), said reaction mixture being cooled in an ice water bath. The resulting mixture was stirred for about 15 hours at room temperature after which time sodium bisulfite was added until the mixture became colorless. The solid product was filtered off, and was recrystallized from methanol to yield a product identified as 1,3-dimethyl-1-(5-methylsulfonyl-1,3,4-thiadiazol-2-yl)urea, having a melting point of about 182°–183° C.

EXAMPLE 5

In a three-necked round bottom flask equipped with a mechanical stirring means and bubbling tube were placed 35.9 of 1-(5-butylthio-1,3,4-thiadiazol-2-yl)-1,3-dimethylurea and 5 g. of ferric chloride hexahydrate in 500 ml. of water. The mixture was cooled to 5° C. and a steady stream of chlorine was bubbled through the mixture for about 20 minutes while maintaining the temperature at 7–9° C. Nitrogen was subsequently bubbled through the mixture to remove excess chlorine. The reaction product mixture was filtered and the solid product recrystallized from aqueous methanol to provide a product identified as 1-(5-butylsulfonyl-1,3,4-thiadiazol-2-yl)-1,3-dimethylurea, having a melting point of about 123°–124° C.

Following the general procedure of Example 5, the following additional compound was prepared and identified by melting point and elemental analyses.

5A. 1-(5-Hexylsulfonyl-1,3,4-thiadiazol-2-yl)-1,3-dimethylurea, having a melting point of about 105°–107° C.

EXAMPLE 6

To a mixture of 200 ml. of anhydrous toluene and 18.8 g of phosgene was added 32.7 g. of 2-methylamino-5-octylthio-1,3,4-thiadiazole and the mixture warmed to about 50° C. and stirred at that temperature for about 2 hours. During this time, anhydrous dimethylamine was passed through the reaction mixture and the temperature rose to about 55° to 60° C. The temperature was held between 50° and 55° C. for an additional 2 hours. The reaction product mixture was cooled and filtered. The filtrate was washed three times with 30 ml.-portions of 6N aqueous hydrochloric acid until the washings were acidic. The organic layer was then washed well with water and dried over anhydrous magnesium sulfate. The drying agent was filtered off and the filtrate concentrated in vacuo to leave an oily residue. The oil was identified by elemental analyses and infrared spectrum as 1,1,3-trimethyl-3-(5-octylthio-1,3,4-thiadiazol-2-yl)urea.

The novel method of this invention is practiced by adding the chemicals to the water containing the aquatic weeds and the algae. The chemicals may be applied as dusts when admixed with a powdered solid carrier such as various mineral silicates, e.g. mica, talc, pyrophyllite, and clays. The chemicals may be mixed with surface-active dispersing agents to form herbicidal and algicidal concentrates to facilitate dispersion in water and to improve the wetting properties when used as sprays. If desired, the chemicals may be mixed with a powedered solid carrier together with a surface-active dispersing agent so that a wettable powder may be obtained which may be applied directly or which may be shaken up with water to make an aqueous dispersion for application in that form. The chemicals may be dissolved in an oil such as a hydrocarbon or chlorinated hydrocarbon oil, and the oil solution of the chemical dispersed in water with the aid of a surface-active dispersing agent to give a sprayable aqueous dispersion. Such surface-active dispersing agents may be anionic, nonionic, or cationic surface-active agents. Such surface-active agents are well known are reference is made to Hoffmann et al., U.S. Pat. No. 2,614,916, columns 2-4, for detailed examples of the same. The chemicals of the present invention may be applied by the aerosol method. Solutions for the aerosol treatment may be prepared by dissolving the chemical directly in the aerosol carrier, which is a liquid under pressure, but which is a gas at ordinary temperature (e.g. 20° C.) and atomspheric pressure, or the aerosol solution may be prepared by first dissolving the chemical in a less volatile solvent, and then admixing such solution with the highly volatile liquid aerosol carrier.

The invention is practiced by adding to the water a sufficient amount of the chemical that a concentration of from about 0.5 to about 10 parts per million is obtained, preferably sufficient chemical to provide a concentration of from about 0.5 to about 2 parts per million.

The optimum concentration for any specific control problem varies with the temperature, the species to be controlled, the sensitivity of the fish life, and the shape of the water body to be treated. At higher water temperatures, less chemical is generally required for a given degree of control than is needed at lower temperatures.

In considering the treatment of moving streams for the purpose of destroying flora fixed therein, special account must be taken of the fact that the chemicals will pass over the area to be treated and that the concentration during the contact period is dependent upon the water flow rate, the rate of chemical addition, and the period of addition.

The novel herbicidal method and compositions are illustrated by the following experiments carried out in the laboratory.

EXPERIMENT 1

In a first test, the plants used were coontail, *Ceratophyllum demersum* L.; Florida elodea, *Hydrilla verticillata* (L.F.); and duckweed, *Lemna minor* L. The plants were prepared by cutting four-inch terminal sprigs of the coontail and elodea, and selecting approximately enough duckweed to just cover the surface of the water in a 10 ml. beaker (approximately 30 plants). The coontail, elodea and duckweed were then placed in beakers containing 750 ml. of dechlorinated water containing the compounds.

The compounds for this test were formulated in the following manner. Seventeen mg. of compound was weighed into a 12 ml. disposable vial. To the vial containing the compound was added 1 ml. of acetone followed by 10 ml. of aqueous 0.1 percent polyoxyethylene sorbitan monooleate. This stock solution was then pipetted into the beakers at volumes of 0.45 ml. and 4.55 ml., to obtain 1 and 10 ppm. concentration of test compound in 750 ml. of water.

Observations of the effect of the compounds on the plants were made over a seven-day period. The scale for rating the aquatic herbicidal activity of the compounds was on a basis of 1-5, as follows:

1 = no effect
2 = slight effect
3 = moderate effect
4 = heavy effect
5 = complete kill The results of the test are recorded in Table 1, which follows.

Where more than one test was conducted, the average of the results was recorded.

Table 1

| Compound of Example No. | Appln. Rate ppm. | Hydrilla | Coontail | Duckweed |
|---|---|---|---|---|
| 1A | 10 | 1 | 1 | 4 |
| 1B | 10 | 5 | 1 | 4 |
| 1C | 10 | 1 | 1 | 4 |
| 1E | 10 | 5 | 5 | 4 |
|    | 1  | 5 | 3 | 4 |
| 1F | 10 | 5 | 5 | 4 |
|    | 1  | 5 | 3 | 2 |
| 1G | 10 | 5 | 3 | 4 |
| 1H | 10 | 1 | 1 | 3 |
| 2  | 10 | 4 | 1 | 4 |
| 2A | 10 | 5 | 3 | 3 |
|    | 1  | 4 | 2 | 2 |
| 2B | 10 | 5 | 2 | 4 |
|    | 1  | 2 | 1 | 1 |
| 3  | 10 | 1 | 1 | 3.3 |
| 4  | 10 | 5 | 2 | 2 |
| 5  | 10 | 5 | 4 | 3 |
|    | 1  | 5 | 2 | 1 |
| 5A | 10 | 5 | 4 | 3 |
|    | 1  | 5 | 4 | 2 |
| 6  | 10 | 5 | 5 | 4 |
|    | 1  | 5 | 3 | 3 |

EXPERIMENT 2

In a second test, the number of plants used in the test was increased to a total of six, and the test was carried out as follows.

Four of the plants to be used in the test, namely Florida elodea, Southern Naiad, Eurasian milfoil, and Cabomba, were prepared by cutting four-inch terminal stems and burying the lower one inch of each stem in a mixture of sterilized sand-clay loam soil (50:50), in plastic 5-oz. drinking cups. The drinking cups containing the plants thus prepared were placed in 1-gallon widemouth jars two weeks prior to testing. Each jar was filled with water to the lower edge of the rim, the volume then being equal to approximately 3500 ml. of water. The water used was dechlorinated city water. There were then added to the top of the water in each jar a four-inch length of coontail, *Ceratophyllum demersum*, and approximately 60 duckweed plants, *Lemna minor* L. In addition, to promote the good growth of the plants, there was added to the water in each jar three drops of a mixture of 5 ml. chelated iron solution, 15 ml. water, and 15 ml. of a commercially available liquid fertilizer.

The following plants were used in this test:
Florida elodea, *Hydrilla verticillata* (L.F.)
Coontail, *Ceratophyllum demersum* (L.)
Duckweed, *Lemna minor* L.
Southern Naiad, *Najas quadalupensis* (Spreng.)
Eurasian milfoil, *Myriophyllum specatum* L.
Cabomba, *Cabomba caroliniana*, Gray
At the end of two weeks, the jars containing healthy preconditioned plants were selected for testing.

The test compounds were formulated in the following manner. Twenty-seven mg. of compound was weighed into a 12 ml. disposable vial. To the vial containing the compound was added 1 ml. of acetone followed by 10 ml. of aqueous 0.1 percent polyoxyethylene sorbitan monooleate. This stock solution was then pipetted into the jars at volumes of 3, 1.5, and 0.75 ml., to obtain 2, 1, and 0.5 ppm. concentration of test compound in approximately 3500 ml. of water. Duplicates were run at each concentration of the compound. Controls to which no test compound was added were also run.

Herbicidal activity ratings were made each week for at least three weeks. The herbicidal activity rating was on a basis of 1–5, as was set forth in the description of Experiment 1, above. When more than one determination was carried out, an average value was calculated for the activity rating.

The herbicidal activity ratings observed the third week are recorded in Table 2, which follows.

Table 2

| Compound of Example No. | Appln. Rate ppm. | Hydrilla | Coontail | Duckweed | Naiad | Milfoil | Cabomba |
|---|---|---|---|---|---|---|---|
| 1E | 5 | 5 | 5 | 5 | 5 | 5 | 5 |
|  | 1 | 5 | 4 | 4 | 5 | 5 | 4 |
|  | 0.1 | 1 | 1 | 1 | 4 | 4 | 2 |
| 1F | 2 | 5 | 5 | 1 | 5 | 5 | 5 |
|  | 1 | 2 | 1 | 3 | 5 | 5 | 1 |
|  | 0.5 | 3 | 3 | 5 | 5 | 5 | 2 |
| 5A | 2 | 5 | 1 | 5 | 5 | 5 | 4 |
|  | 1 | 5 | 2 | 5 | 1 | 5 | 2 |
|  | 0.5 | 3 | 2 | 1 | 2 | 3 | 4 |
| 6 | 2 | 5 | 5 | 4 | 5 | 5 | 5 |
|  | 1 | 2 | 1 | 1 | 3 | 3 | 1 |
|  | 0.5 | 1 | 1 | 1 | 3 | 3 | 4 |

The tests show the practice of the novel method of this invention controls aquatic weeds.

I claim:

1. A method of destroying aquatic weeds in water which comprises contacting the weeds with an herbicidally-effective amount of a compound of the formula

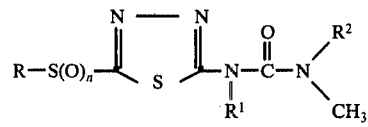

wherein
R is $C_1$–$C_8$ alkyl, $C_3$–$C_7$ cycloalkyl, benzyl or phenethyl
$R^1$ is methyl or ethyl;
$R^2$ is hydrogen, methyl or ethyl; and
$n$ is 0, 1 or 2.

2. The method of claim 1 wherein the herbicidally-effective compound is of the formula

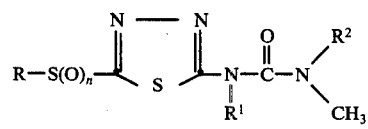

wherein
R is $C_4$–$C_8$ alkyl;
$R^1$ is methyl;
$R^2$ is hydrogen or methyl; and
$n$ is 0 or 2.

3. The method of claim 1 wherein the herbicidally-effective compound is of the formula

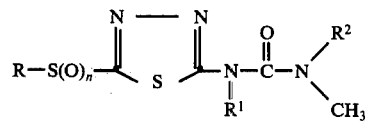

wherein
R is $C_6$–$C_8$ alkyl;
$R^1$ is methyl;
$R^2$ is hydrogen or methyl; and
$n$ is 0 or 2.

4. The method of claim 1 wherein the active compound is 1-(5-hexylthio-1,3,4-thiadiazol-2-yl)-1,3-dimethylurea.

5. The method of claim 1 wherein the active compound is 1,1,3-trimethyl-3-(5-octylthio-1,3,4-thiadiazol-2-yl)urea.

6. The method of claim 1 wherein the active compound is 1,3-dimethyl-1-(5-octylthio-1,3,4-thiadiazol-2-yl)urea.

7. The method of claim 1 wherein the active compound is 1-(5-hexylsulfonyl-1,3,4-thiadiazol-2-yl)-1,3-dimethylurea.

8. The method of claim 1 wherein the herbicidally-effective amount of the active compound is from 0.5 to about 10 ppm.

* * * * *

UNITED STATES PATENT OFFICE
CERTIFICATE OF CORRECTION

Patent No. 4,056,382                      Dated   November 1, 1977

Inventor(s) Quentin Francis Soper

It is certified that error appears in the above-identified patent and that said Letters Patent are hereby corrected as shown below:

Column 3, line 3:   "weels" should read --weeds--.

Column 3, line 60:  "$(C_1-C_3)$" should read --$(C_1-C_2)$--.

Column 10, line 10:  "ethyl" should read --ethyl;--.

Signed and Sealed this

Twenty-first Day of March 1978

[SEAL]

Attest:

RUTH C. MASON
Attesting Officer

LUTRELLE F. PARKER
Acting Commissioner of Patents and Trademarks